United States Patent [19]

Adelson

[11] Patent Number: 5,068,523

[45] Date of Patent: Nov. 26, 1991

[54] SCANNER DETECTOR ARRAY AND LIGHT DIFFUSER

[75] Inventor: Alexander Adelson, Peekskill, N.Y.

[73] Assignee: Intec Corp., Trumbull, Conn.

[21] Appl. No.: 487,571

[22] Filed: Mar. 2, 1990

[51] Int. Cl.$^5$ .................... H01J 40/14; G01N 21/88
[52] U.S. Cl. ............................ 250/208.1; 250/572; 250/236
[58] Field of Search ............... 250/572, 236, 235, 234, 250/208.1, 571, 578.1; 356/431, 430; 350/6.8

[56] References Cited

U.S. PATENT DOCUMENTS

| | | | |
|---|---|---|---|
| 3,814,946 | 6/1974 | Takahashi et al. | 250/572 |
| 4,038,554 | 7/1977 | Craig | 250/572 |
| 4,172,666 | 10/1979 | Clarke | 356/431 |
| 4,431,309 | 2/1984 | Sick et al. | 356/431 |
| 4,500,208 | 2/1985 | Sick | 250/572 |
| 4,634,281 | 1/1987 | Eikmeyer | 356/431 |
| 4,644,411 | 2/1987 | Sato et al. | 250/208.1 |
| 4,680,644 | 7/1987 | Shirato et al. | 250/208.1 |
| 4,697,082 | 9/1987 | Bartelsen | 356/431 |
| 4,914,309 | 4/1990 | Masaharu et al. | 250/572 |

Primary Examiner—Davis L. Willis
Assistant Examiner—Michael Messinger
Attorney, Agent, or Firm—Sprung, Horn, Kramer & Woods

[57] ABSTRACT

A detector for a laser scanner has an array of detector elements disposed in at least one row and side-by-side in a plurality of columns, wherein each detector element comprises a lens receptive of laser light on one face thereof along a light path from the target and outputting light at the other face. The detector elements also include a photodetector for generating an electrical signal in response to light received thereon. The photodetector is mounted at a fixed distance from the other face of the lens and facing the other face to receive light passing through the lens and a preamplifier is mounted adjacent the photodetector on a common substrate for receiving the signal generated thereby.

7 Claims, 3 Drawing Sheets

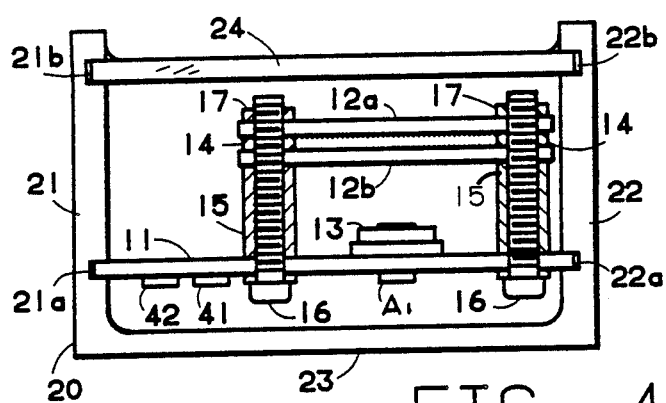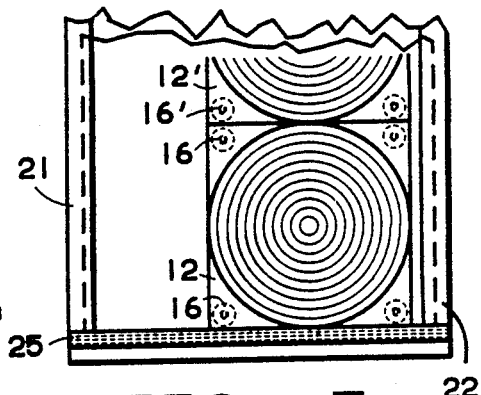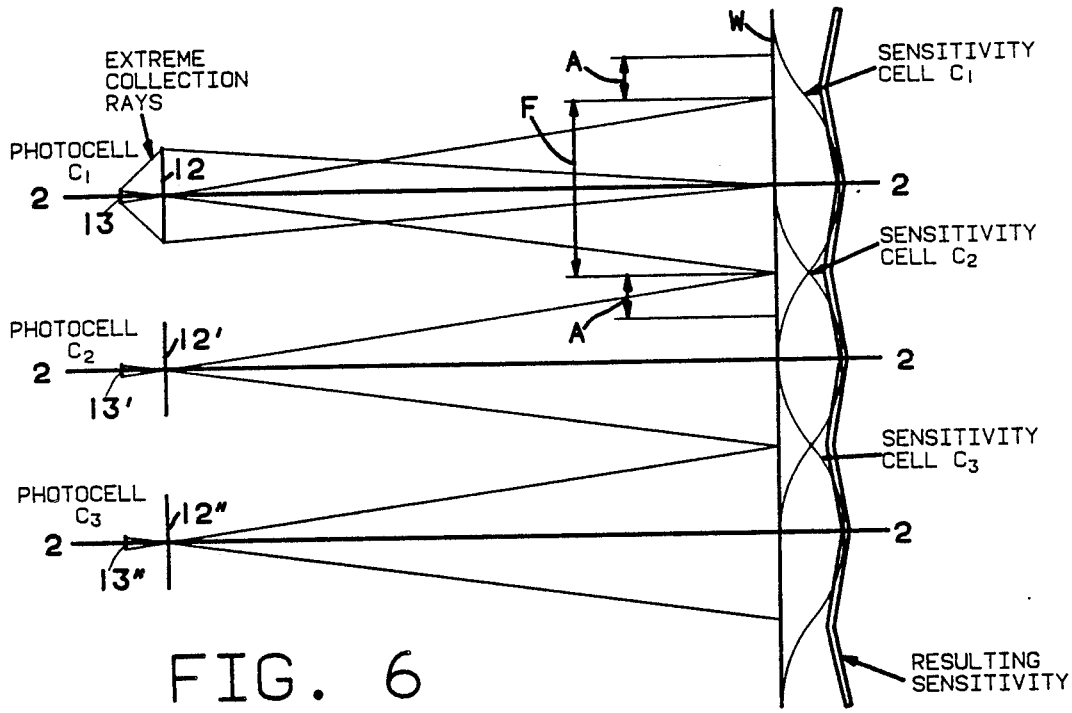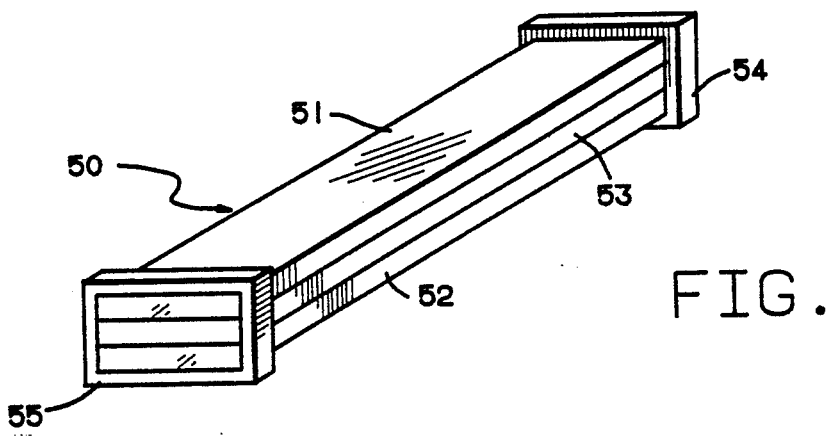

SCANNER DETECTOR ARRAY AND LIGHT DIFFUSER

BACKGROUND OF THE INVENTION

The present invention is directed to a detector for light detection for use in devices such as a scanner, and in particular a detector for a scanner using a high energy light source such as a laser, which is capable of scanning a relatively wide web moving at a high speed.

A laser scanner for scanning a wide moving web, that is, a web on the order of greater than 0 to 60" moving at speeds of up to at least 1200 feet per minute is disclosed in the applicant's copending application Serial No. 487,572 filed Mar. 2, 1990.

In a scanning system of that type, the scanner generates a scan line, which is greater than 50" long, across the web and a receiver or detector collects the energy which is either reflected by the web or which passes through the web, generates a signal corresponding thereto, amplifies and conditions the signal and then sends the signal to a control computer where it is analyzed by comparing it with preset thresholds. If the signal from a given point on the scan line exceeds the threshold, an object is reported. One such object is a flaw in the case of a scanner used in a flaw detection system. If the signal is lower than the preset threshold, there is no reported object.

The resolution of the system depends not only on the scanning spot size, but on the response speed of the receiver and the receiver speed is determined by the speed of the photodetector therein and the associated processing circuitry.

In a detector for such a system, there are limitations. High speed electronics yield higher levels of random noise which can cause false triggering in the threshold circuitry. Moreover, there is a tradeoff between speed and cost since certain types of photodetectors are costly, and this cost is multiplied when numerous photodetectors or exotic photodetectors such as photomultipliers are needed to detect light energy from a relatively wide web.

SUMMARY OF THE INVENTION

The main object of the present invention is to provide a detector consisting of both optical and electronic components which is economical in cost, while preserving the required performance sensitivity levels and resolution requirements for detecting an object such as a flaw on a web moving at speeds of up to 1200 feet per minute or greater with widths of up to 60" or more.

Another object of the present invention is to provide a detector with a Fresnel optical train enabling a small size with a high collection efficiency.

A further object of the present invention is to provide a detector with a Fresnel optical train which enables a modular optoelectronic configuration.

A still further object of the present invention is to provide a parallel preamplifier circuit which enables a low noise, broad band, high speed response.

Still another object of the present invention is to provide a detector with a light diffuser which suppresses the lens signature in the direct transmission of energy through a target.

These and other objects and advantages of the present invention are achieved in accordance with the present invention by the use of novel and efficient collecting optics and constructing the electronics and optics to achieve a high signal to noise ratio.

In accordance with the invention, the photodetector is preferably a photodiode which is fast enough to accommodate the resolution required in the system and is relatively inexpensive. While fast photodiodes are small in area, the ability to obtain a detecting width of up to 60" is achieved by utilizing a collecting lens spaced from the surface of the photodiode. Preferably, the collecting lens spaced from a photodiode surface having a width of less than 10 mm.

The tradeoffs involved in designing the lens-photodiode assembly result in further preferred embodiments of the invention. As the lens moves away from the web, the photodiode is able to see a larger width of the web, however this causes a decrease in signal amplitude. While the lens diameter of the collecting lens can be increased, the focal length of the lens will grow which increases the distance between the photodiode and the lens. The increase in this distance will decrease the field of view which is undesirable.

As a result, the detector preferably uses a Fresnel lens as the collecting lens and in particular a pair of Fresnel lenses. The Fresnel lenses preferably have a value of f #=0.5-1.0.

A further feature of the present invention is the mounting of the preamplifier adjacent the photodetector for receiving the signal generated by the photodetector. In a preferred embodiment according to the present invention, the photodetector and preamplifier are mounted on a common substrate. In another preferred embodiment, the array of detector elements comprises one detector module having a plurality of lenses mounted side by side and the photodetectors and preamplifiers for all of the lenses in the module are mounted on the same common substrate.

The detector modules are preferably mounted in a U-shaped frame having a laser transparent window at an open side thereof which preferably acts as a filter to keep out ambient light.

The photodetector preferably has a surface diameter of approximately 0.36" and the Fresnel lenses preferably have a diameter of approximately 2" and are spaced approximately 625" from the photodetector.

In an embodiment wherein light passes through the web to be detected, the detector preferably comprises light diffusing means disposed along the light path between the web and the detector lenses for diffusing light from the web. The lens array is mounted angularly displaced from the light path by an angle 8 such that the light energy received by the lenses is cosine 8 times the light energy from the diffuser.

As a result of this structure, the "signature" associated with a direct scan spot incidence on the detector is eliminated.

These and other embodiments of the present invention will be more completely described in the following detailed description taken with the attached drawings, wherein:

BRIEF DESCRIPTION OF THE DRAWINGS

FIG. 4 is a sectional view of the detector module of FIG. 3 mounted in a frame according to the present invention;

FIG. 5 is a top view of the structure of FIG. 4;

FIG. 6 is a graphical representation of the sensitivity of the detector according to the present invention;

FIG. 7A is a detail of the diffusion window of FIG. 7;

DETAILED DESCRIPTION OF THE INVENTION

Figure 1:
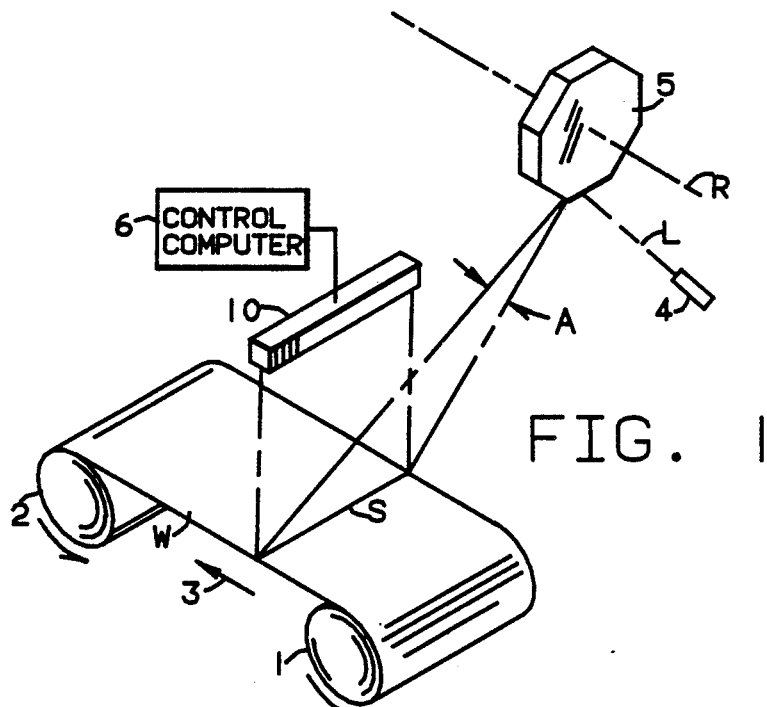
FIG. 1 is a schematic representation of a system using the detector according to the present invention.

It is noted that like reference numerals refer to the same structure in each of the figures.

Referring now to FIG. 1, a scanning system comprises a laser source 4, preferably a helium neon laser tube or a semiconductor laser diode generating a laser beam having a wavelength of 400 to 820, preferably 780 nM, which is aimed at a rotating scanning element 5 which rotates about an axis of rotation R to scan a beam scan line S which is perpendicular to axis of rotation R and which includes an angle A. The scan line S is scanned across a moving web W which moves from a supply roll 1 to a take-up roll 2, with rolls 1 and 2 rotating such that the direction of transport of the web W is in the direction of arrow 3. The scan line S is preferably perpendicular to direction 3 as shown. A detector 10 according to the present invention receives light reflected from web W to collect energy. It should be noted that the collector 10 is particularly suited for webs having a width of from 40 to 60" where the scan line S extends 40 to 60" in length. However, the detector according to the present invention can be of any desirable width from 1" to 60" and can be used to detect energy from stationary targets as well as moving targets such as a moving web W and to detect any type of object on a target, although it preferably detects flaws in a moving web of material.

The detector 10 produces an electrical signal corresponding to the detected energy and the signal is then passed to a control computer 6 which compares the signal to predetermined thresholds in order to determine if an object has been detected on the target and the type of object that has been detected. The control computer can be any suitably programmed 80286 or 80386 IBM PCAT compatible computer or better.

Figure 2:
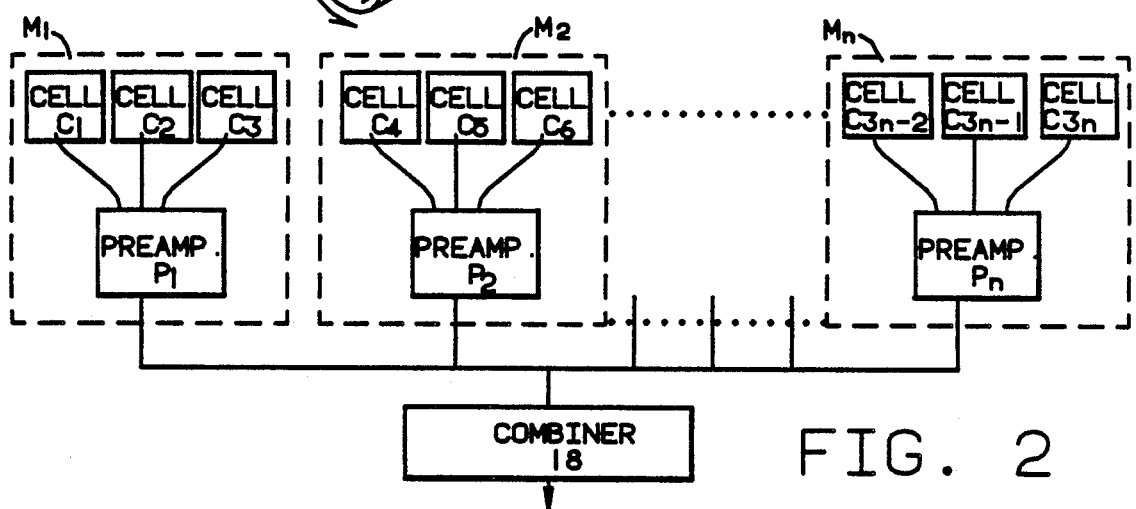
FIG. 2 is a block diagram of the electronics of the detector of FIG. 1.

As shown in the block diagram of FIG. 2, the detector 10 according to the present invention preferably consists of a plurality of detector modules $M_1$, $M_2$ and $M_n$. Each detector module M comprises three cells, each cell including a photodiode 13 and a collector lens 12. The modules $M_1$-$M_n$. include cells $C_1$-$C_{3n}$. Each module includes the three cells C connected in turn to a preamplifier P so that modules $M_1$-$M_n$ have preamplifiers $P_1$-$P_n$. All of the preamplifiers P are connected to a combiner 18 and the output of the combiner is fed to the control computer 6.

Figure 3:
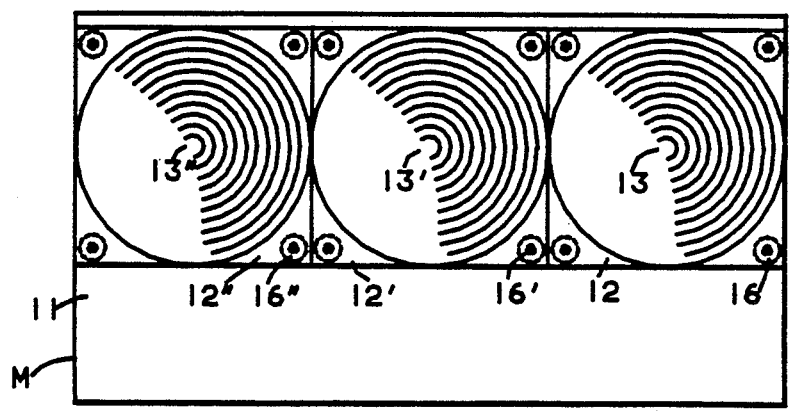
FIG. 3 is a top view of one detector module according to the present invention.

FIGS. 3-5 show the construction of each module M according to the present invention.

As shown therein, the module M consists of a printed circuit board 11 which is common to the three cells. The three cells include three collecting lenses 12, 12' and 12", each preferably consisting of a pair 12a, 12b of Fresnel lenses spaced apart by spacers 14 and mounted by means of mounting screws 16 and spacing posts 15 at a fixed distance from the printed circuit board 11. Alternatively an optical equivalent of the Frensnel lenses can be used for lens 12. Also mounted on the printed circuit board 11 are three photocells 13, 13', 13" disposed centrally of the lens 12, at a fixed distance from the lens, which is preferably 0.625", to receive energy collected by the lens 1 focusing thereon. Mounted immediately adjacent to the cells is the preamplifier P. The closeness of the mounting of the preamplifier to the cells ensures that very little noise will enter the system and that the signal to noise ratio will remain high. The combiner 18 is disposed on a separate printed circuit board to receive outputs from the various preamplifiers $P_1$-$P_n$.

Each module M preferably has three detectors disposed side by side in a line as shown in FIG. 3. Each lens 12, 12', 12" is a two inch square so that the width of the module M is 6". Therefore, in order to obtain a detector having a width of 84", 14 of the modules M are disposed side by side in a row. As shown in FIG. 4, this mounting of the modules in a row is accomplished by means of a U-shaped bracket 20 having two arms 21, 22 and a base 23 connecting the arms so that there is an open face formed thereby.

Sides 21, 22 have grooves 21a, 22a and 21b, 22b formed therein as shown in FIG. 4. Grooves 21a and 22a form a guide for receiving the edges of the printed circuit board 11 of each module so that the U-shaped member having a length of up to 84" can accommodate 14 modules $M_1$-$M_{14}$ in a single row. The guide formed by grooves 21b and 22b receives a light transmissive window member 24.

The window 24 can be glass or plastic and is preferably filtered to remove ambient light. In the case where the laser light sources are 780 nM lasers, a red plastic that exhibits an aggressive blocking characteristic in the visible region is preferred.

Figure 8:
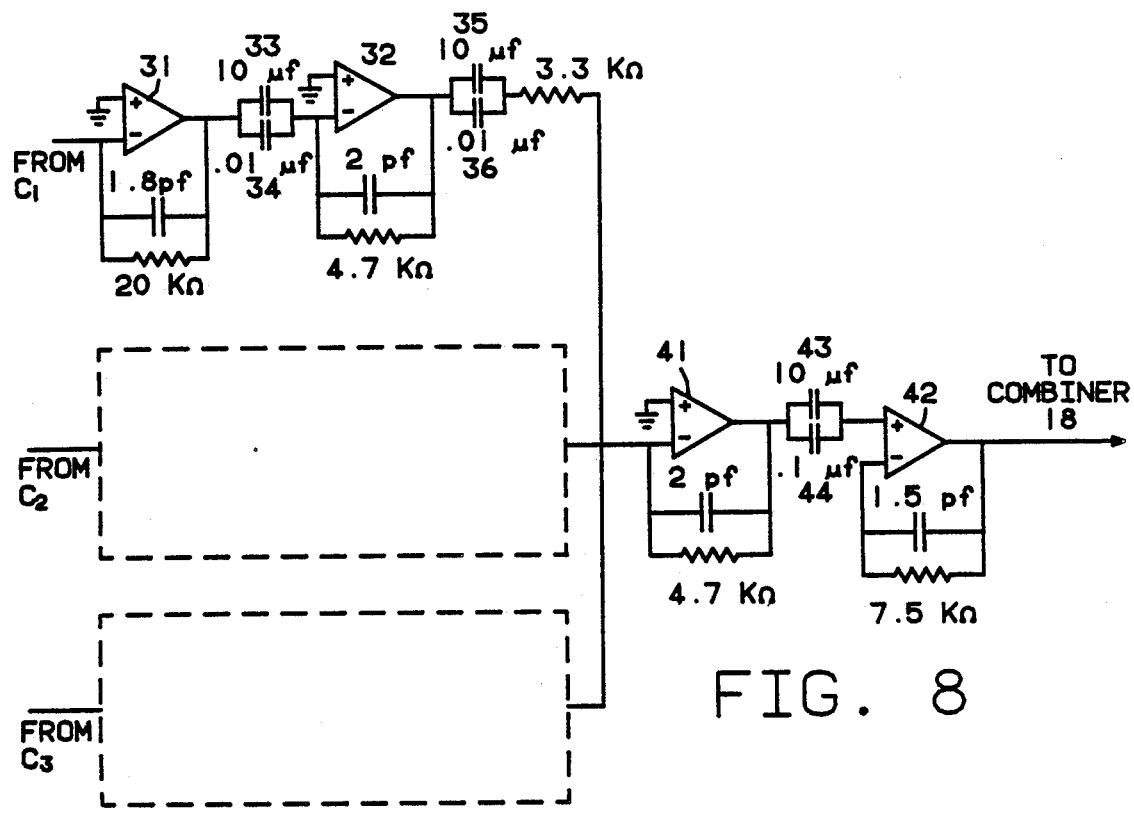
FIG. 8 is a schematic diagram of the preamplifier circuit shown in FIG. 2.

Each preamplifier P on one module is formed entirely on the common printed circuit board adjacent the photodetector in order to maintain high signal to noise ratio. FIG. 8 shows the circuitry for one preamplifier $P_1$ for cells $C_1$-$C_3$.

The preamplifier P is built around a high speed Norton amplifiers 31, 32, which are preferably an LM359 by National Semiconductor. There are three identical channels $A_1$-$A_3$ on the board 11 and only one is shown in detail for the purposes of clarity. The input of each channel is connected to the output of one photodiode 13, 13', 13". The output of the three channels are then combined in one summing amplifier stage 41. There is one last stage 42 following the summer 41 and coupling capacitors 43, 44 which acts a driver for driving an output to the combiner 18.

The preamplifier circuit operates as follows. Laser energy collected by the Fresnel optics 12 is converted into an electrical current by the high speed photodiode 13. This current signal is amplified and converted to an AC voltage which is superimposed on a DC level by Norton amplifier 31. The signal is now coupled to a second Norton amplifier stage 32 via capacitors 33 and 34, one providing a good low frequency response characteristic while the other maintaining high frequency gain accuracy. Capacitive coupling is necessary here so as not to disturb the DC biasing of the following amplifier stage 32.

The signal at the output of the second stage is again AC coupled via capacitors 35 and 36 to the summing amplifier 41. This stage takes the output of all three photodiode channels and sums them together. This is an inverting amplifier with a voltage gain of about 3 db. The output of this stage is capacitively coupled to line driver 42 via capacitors 43, 43.

Figure 9:
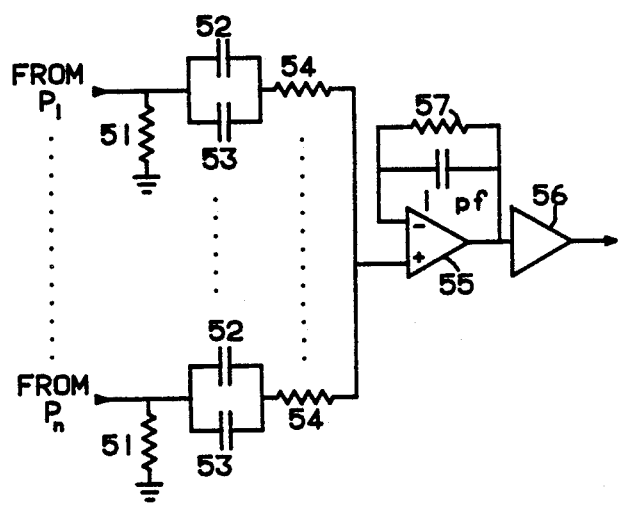
FIG. 9 is a schematic diagram of the combiner circuit shown in FIG. 2.

FIG. 9 shows the circuitry for combiner 18. The signals from the preamplifiers are brought down to one input connector which is terminated with a 68 ohm resistor 51 which is the same for each preamplifier to provide a close match to the characteristic line impedance. The signal is AC coupled via capacitors 52, 53 into a summing stage 55 (LM 359). The gain of the stage is set by the ratio of the input resistor 54 to the feedback resistor 57 and is approximately 2.

The output of the summing amplifier 55 is now used to drive a wideband current driver 56 for which a National Semiconductor LH4001 is used. The output of driver 56 is fed to computer 6.

In a preferred embodiment of the present invention, the configuration of the lenses and the photocells are set to maximize the sensitivity across the field of view of the detector. As shown in FIG. 6, a graphical representation has been made to show the sensitivity achieved by the detector according to the present invention. The distribution of sensitivity across the field of view F for each cell varies with the signal amplitude which is function of the distance from the collecting lens. The maximum signal is achieved along the axis Z shown in FIG. 6 and the effective field of view is at the point where the signal amplitude is 50%. As shown in FIG. 6, the angles for the field of view are drawn to coincide with the sensitivity for each cell at its 50% point. Thus the most effective way to cover the web is to locate the individual collecting cells including the photodiode and lens in such a way that the points are 50% intensity levels of two neighboring cells coincide with the collection plane as is shown in FIG. 6. The resulting sensitivity is approximately uniform across the entire web as is shown in FIG. 6.

Furthermore, since it is desirable to keep magnification of the object at the smallest practical level, which is ideally 1:1, this ratio is approached but not reached as one reduces the field of view sensitivity to a minimum. The photocell according to the present invention has an appropriate rise time and has a useful sensitive area of approximately 0.320" by 0.150". The lens is preferably a Fresnel lens pair with a diameter of 2" and a focal length of 1". Thus the field of view size on the web W equals 3" with 2" dedicated to the 50% intensity level field of view F shown in FIG. 6 and ½" of overlap A on each side for the overlapping of field of views. Therefore, to cover a 50" wide web, 25 cells are needed.

Figure 7:
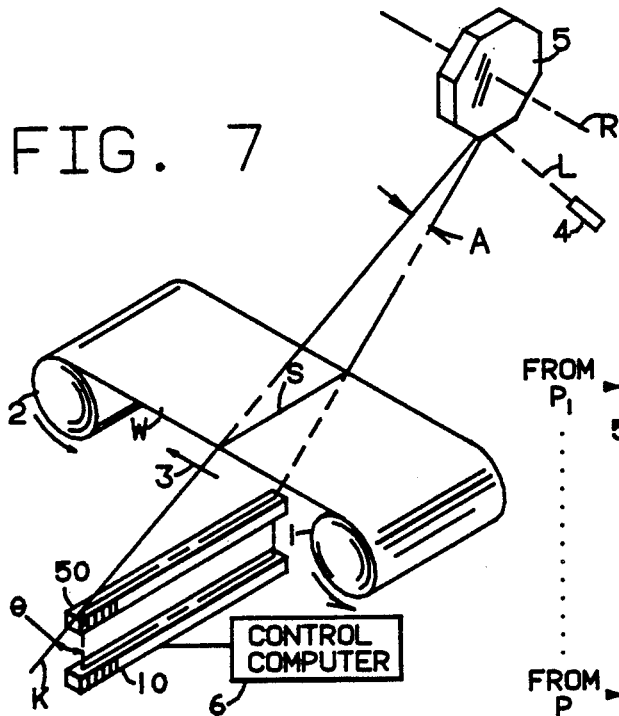
FIG. 7 is a schematic representation of a scanning system utilizing a detector and a diffusion window according to the present invention.

FIG. 7 illustrates another embodiment of the present invention wherein a transparent target or web W is used or where the target to be found in the web is transparent such as a hole in a web and the detector and scanner are located on opposite sides of the web as shown in FIG. 7.

When dealing with through the web detection, a problem that results is the presence of a "signature" associated with the direct scan spot incident on the detector. This is not a problem in the embodiment shown in FIG. 1 when there is a wide dispersion of the light due to the reflection of the web. In a through the web detector, and in the detector of FIG. 1 when a web surface is dominated by a specular reflective component, the energy is not dispersed but rather focused as it scans across the detector and this causes the detector boundary conditions to become part of the signal producing a totally objectionable signature, and reducing parts of the scan as unusable.

In order to solve this problem, a diffusion window 50 is located about 1" from the target on the optical axis thereof. The detector 10 is then positioned not on the optical axis K, but rather it is displaced by approximately ½ the lens diameter or greater, that is, about ½" or more producing an optical path at an angle Θ to optical path K. By shifting the detector from the beam path, the detector is shifted away from the central rays. These central rays are eliminated instead of dominating the light transmitting through the diffusers. As a result, the energy from the diffusion window 50 is seen by the detector 10 varying by the cosine of the angle Θ. The angle Θ is $0° < \Theta \leq 45$ and is preferably about 7°. Therefore the energy is spread over the collection window eliminating the signature. The diffusion window would be placed above the web in the embodiment of FIG. 1.

The diffusion window 50, as shown in FIG. 7A, comprises two glass plates 51, 52 with a Lambertian diffuser 53 therebetween. The layers are held together by frame members 54, 55. Diffuser 53 can be ground glass, milk glass, opal glass or preferably mylar drawing film.

It will be appreciated that the instant specification and claims are set forth by way of illustration and not limitation, and that various modifications and changes may be made without departing from the spirit and scope of the present invention.

What is claimed is:

1. A detector comprising: an array of detector elements disposed in at least one row and in a plurality of columns, wherein each detector element comprises a lens receptive of light on one face thereof along a light path from a target and outputting light at the other face, a photodetector for generating an electrical signal in response to light received thereon, for receiving the signal generated by the photodetector, wherein the array of detector elements comprises at least one detector module having means mounting a plurality of lenses side-by-side, a common substrate on which the photodetectors and preamplifiers for all of the lenses in the module are mounted with each preamplifier adjacent to a corresponding photodetector, means mounting the common substrate in the at least one detector module comprising a U-shaped frame having a light transparent window at an open side thereof and slots for slidably receiving the common substrate parallel to the window and means connecting the plurality of side-by-side mounted lenses to the common substrate to dispose each photodetector at a fixed distance form the other face of a corresponding lens and facing the other face to receive light passing through the lens.

2. The detector according to claim 1, further comprising light diffusing means disposed along the light path between the target and the lenses for diffusing light form the target and means mounting the array angularly displaced from the light path by an angle Θ, such that the only light energy received by the lenses is cosine Θ times the light energy from the diffuser.

3. The detector according to claim 1, wherein each lens comprises Fresnel lens.

4. The detector according to claim 3, wherein the photodetector has a surface diameter of approximately 0.36", the Fresnel lenses have a diameter of approximately 2" and are spaced 0.625" from the photodetector.

5. The detector according to claim 1, wherein each lens comprises a Fresnel lens pair.

6. A detector comprising an array of detector means each having a collecting lens and a photodetector receptive of light form a target along a light path; light diffusing means disposed along the light path between the target and the collecting lenses for diffusing light from the target; and means mounting the array angularly displayed from the light path by an angle $\Theta$, wherein $0° < \Theta \leq 45°$, such that the only light energy received by the collecting lenses is cosine $\Theta$ times the light energy from the diffuser.

7. A method comprising: scanning light along a light path at a target and detecting the light from the target with at least one collecting lens by disposing a light diffuser along the light path between the target and the at least one collecting lens to diffuse light form the target and angularly displacing the at least one collecting lens for the light path by an angle $\Theta$, where $0° < \Theta \leq 45°$, such that the only light energy received by the at least one collecting lens is cosine $\Theta$ times the light energy from the diffuser.

* * * * *